United States Patent [19]

Siegel

[11] Patent Number: 4,730,849

[45] Date of Patent: Mar. 15, 1988

[54] MEDICATION DISPENSING IDENTIFIER METHOD

[75] Inventor: Harold B. Siegel, Clearwater, Fla.

[73] Assignee: Seigel Family Revocable Trust, Clearwater, Fla.

[21] Appl. No.: 11,018

[22] Filed: Feb. 5, 1987

[51] Int. Cl.⁴ .................. B42D 15/00; G09C 5/00; G09C 1/04; G06F 15/42

[52] U.S. Cl. .................. 283/70; 283/75; 283/81; 364/413

[58] Field of Search ............ 283/18, 19, 21, 70, 283/81, 112, 75, 81; 40/306, 312, 493; 364/400, 412, 413, 415; 358/93, 903; 273/1 GC, 1 E, DIG. 28; 209/547

[56] References Cited

U.S. PATENT DOCUMENTS

| | | | |
|---|---|---|---|
| 2,105,367 | 1/1983 | Parsons | 283/81 |
| 3,848,112 | 11/1974 | Weichselbaum et al. | 364/413 |
| 4,276,570 | 6/1981 | Burson | 358/903 |
| 4,312,523 | 1/1982 | Haines | 283/81 |
| 4,386,795 | 6/1983 | Charles et al. | 283/70 |
| 4,521,014 | 6/1985 | Sitrick | 273/DIG. 28 |

Primary Examiner—E. R. Kazenske
Assistant Examiner—Paul M. Heyrana, Sr.
Attorney, Agent, or Firm—Lawrence P. Benjamin

[57] ABSTRACT

A method of maintaining a close surveillance over and the monitoring of the dispensing of prescribed medication, to insure that the proper patient is, in fact, being administered the prescribed medication and dosage, and that the patient for whom the medication is prescribed is properly identified or recognized, before medication is administered. To assure that the proper patient is receiving the prescribed medication, both a photograph and a desription of the medication and dosage is imprinted on a label affixed to a means for transporting the medication to the patient. The label may also contain other vital patient information such as patient allergies and any anticipated adverse reactions to the medication and other instructions for the well being of the patient.

4 Claims, 3 Drawing Figures

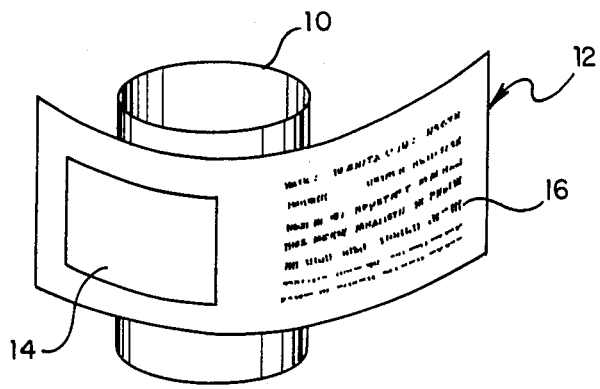
FIG. 1
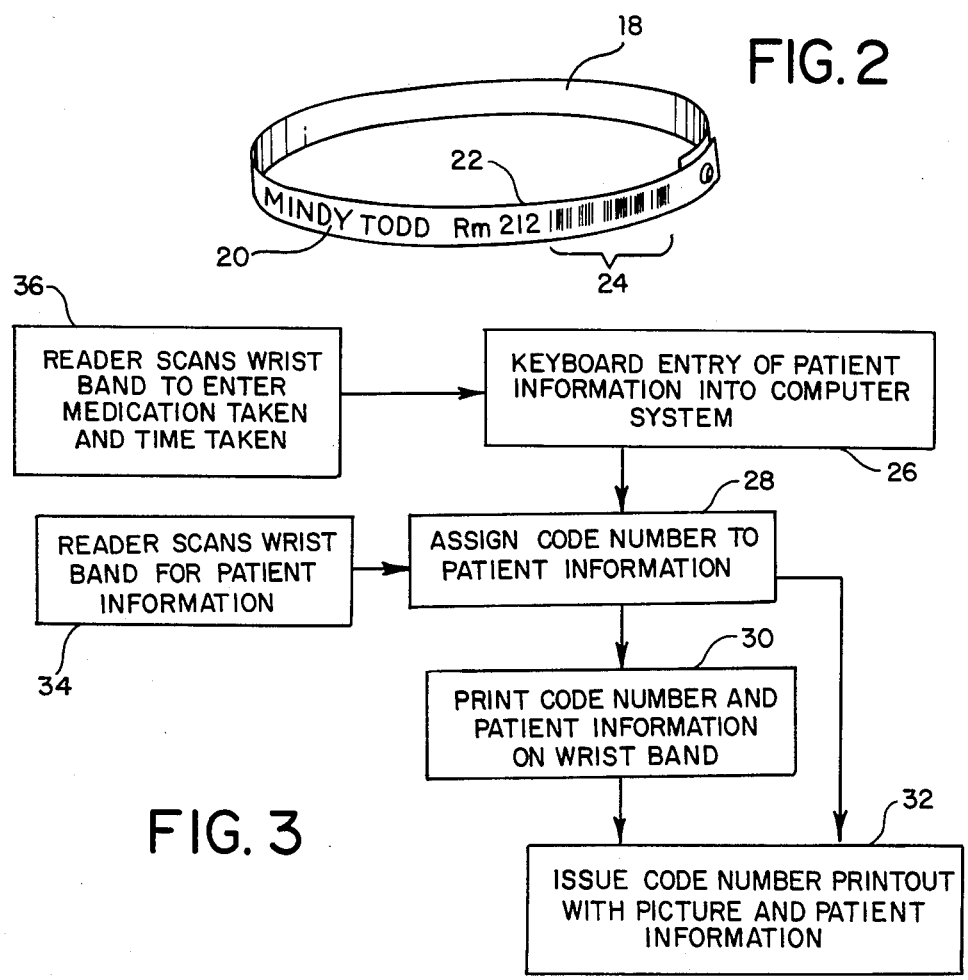
FIG. 2
FIG. 3

MEDICATION DISPENSING IDENTIFIER METHOD

FIELD OF THE INVENTION

This invention relates, in general, to both a system and an associated process for the proper identification of medication, and more particularly to the use and the application of particular unique indicia to any one of a number of medication dispensing containers to assure that only the patient for whom the the medication was prescribed, will receive only his medication.

BACKGROUND OF THE INVENTION

It has become increasingly apparent that, with the rising numbers of elderly people requiring frequent medication, and with the increasing reliance of the medical profession, on occasion, to dispense a plurality of drugs to alleviate specific symptoms, extreme care must be exercised in order that the patient receive the prescribed medication. To further complicate the present situation of elderly people residing in rest homes or convalescent centers, the duty of dispensing the medication frequently falls on inexperienced, and often under paid orderlies or unpaid volunteers who often lack the professionalism of a registered nurse and thus, could not thus assure that the patient will receive the proper and required medication in a timely fashion.

One medication prescreening method, that is a common and accepted practice in the medical services profession, requires that a nurse, or other professional, prepare a tray with, for example, the patients name and room number written on a slip of paper to be included on the tray. The prescribed medication, usually in a cup or other suitable container, is then brought to the patient to whom the medication is dispensed, in accordance with the instructions issued by the prescribing physician. The physician usually relies on the nurse to further observe the patient to see if there have been any untoward side effect brought on by the medication. The instructions are usually left at the attending nurses station on the patients chart. If the doctor anticipates an allergic or adverse reaction to the prescribed drug or a combination of drugs, this too will be noted for the attending nurse who will be asked to observe any patient reaction, and to take an appropriate action. This mode of operation may be adequate for those situations where the nurses work load is sufficiently small and all of the patients are known to and are recognized by the person dispensing the medication.

In the situations where the patient-recipient, to whom the medication is to be dispensed, is not known to the nurse or orderly, or where the nurses work load is sufficiently heavy so as to introduce an element of unfamiliarity or lack of acquaintance with both the patient-recipient and the medication the patient is required to have, then there is the possibility that the patient will not receive the medication intended and instead, will receive the medication intended for another. Obviously, this situation must be avoided at all costs.

SUMMARY OF THE INVENTION

The subject medication dispensing identifying system, and an associated method of implementing the system is directed to a close and accurate surveillance of both the medication and the person to whom the medication is dispensed. This may be done, in one embodiment, by affixing a photograph of the patient to either (or to both) the container, in the form of a label, or may be affixed to the patient medication card, divider card, medication storage segments, chart, records card, or any combination of the above, in order to assure both the patient, the doctor and the nurse, that the patient is, in fact, receiving the correct medication.

In another embodiment, when the patient is admitted and a non-removable identifying wrist band is initially issued, the wrist band will have a distinctively coded, machine readable portion imprinted thereon and, if desired, it may also include a computer generated likeness or a miniature photograph of the patient. In addition to having the usual information printed on the wrist band, such as the name of the patient, date of admission and etc., a coded portion may include other information vital to the well being of the patient. This coded information may list known allergies or adverse drug reactions, the name of a person to be notified in the event of an emergency, or an unlisted telephone number for the attending physician as well as a coded photograph of the patient. The coded information may easily be stored in a computer bank for easy and quick retrieval.

BREIF DESCRIPTION OF THE DRAWING

FIG. 1 details one embodiment of my novel medication dispensing identifier indicating a typical label which may be attached to either a dispensing vial, as shown, or affixed to a medication card or other medication storage segment;

FIG. 2 is one embodiment of my novel identifier indicating how the code number identifier is applied to a typical hospital wrist band; and, FIG. 3 is a flow chart of an operative embodiment of my novel medication dispensing identifier, setting forth an improved, cost effective and time saving method that will achieve fool proof and positive patient identification during medication dispensing.

DETAILED DESCRIPTION OF ONE EMBODIMENT OF THE INVENTION

The expression "code number", as hereinafter used, refers to any distinctively coded, machine readable data and is meant to include any one, or any combination of the following: numbers that have been printed with magnetic ink; any "bar code" system such as the vertically arranged, parallel bars, used in supermarkets to identify the various items for sale; the bars used by the Postal Service to designate the various ZIP codes; any concentrically arranged circles forming a "bulls eye", as well as any other coded data, provided it is in a machine readable format.

Referring now to FIG. 1, there is depicted an example of a label 12, that might be affixed to a vial 10 or any other means for containing medication for a patient. A portion of label 12 has photograph 14 imprinted thereon, while information portion 16, occupying the remainder of label 12, is imprinted with any required vital information that may relate to possible allergic patient reactions to the drug or medication being administered, as well as any other symptom that should be monitored by the nurse.

It will be understood by those skilled in the nursing and medical professions that the proposed information listed above is given by way of example and it is not intended to be limited solely to the examples mentioned.

The above information should ideally be obtained from the patient and the attending physician upon admission of the patient into the care facility and stored in a computer memory bank for future use. Once the vital information is obtained and stored, the patient and the vital information may then be identified by a distinctive, machine readable code number that may be in the form of a bar code, for example, and each time it is desired to access the computer for the patient history of allergy reactions, one merely has to enter the patients code number or even his name, and a printout to the patients vital information history as well as a computer generated photographic likeness is immediately available in the form of a printout. This may be easily accomplished by inserting an appropriate machine bar code on the typical, plastic wrist band. As shown in FIG. 2, a wrist band 18 has the name of the patient 20, the patients room 22 and the code number 24 imprinted thereon. Thus, any time that the patient information is needed, such as in an emergency, it is merely necessary to bring a portable bar code reader to the patient, scan the code number on his wrist band and, in a matter of seconds, a printout will be obtained. Such emergency may arise, for example, when a patient becomes severely disoriented and wanders away from his room to an unfamiliar part of the facility. Any nurse would be able to read the bar codes on the wrist band of the disoriented patient and quickly determine who he is, where he should be and who should be notified.

In any event, the bar code information serves the additional function of monitoring the timely dispensing of the medication by having the bar code scanned and an additional coded input made to the computer indicating that the medication has been dispensed, at which time, the computer may enter the time and date in order to keep track of both the time and the cumulative dosage of the drug.

Referring now to FIG. 3, there is shown a flow chart of one embodiment of a medication identifier and monitoring system to achieve optimum results for both identifying the patient and for assuring that the patient will be administered the correct dosage of indication, at the proper time and that an accurate record will be kept of the cumulative dosage. This is done initially by making a keyboard entry 26 of the patient information at the time the patient is admitted, or if the patient had previously been at the facility, the earlier obtained data is updated to include any new information that may now be pertinent. This keyboard entry enters the information into the computer system memory bank. A photograph is then taken of the patient that is scanned and, as is well known in the art, the photographic information thus obtained is converted to machine language that is able to reproduce the photograph on demand. This photographic data, together with the previously obtained patient information is assimilated by the computer and converted into a code number (in both alpha numeric form as well as a bar code) that is assigned 28 exclusively to the patient. Once the code number is determined, the code number, in bar code form, is imprinted 30 on a wrist band together with other data, such as the name of the patient, the room number and etc., (FIG. 2). An initial code number printout is then generated 32 in both alpha numeric and bar code form, with patient information and a copy of the patient photograph, (FIG. 1).

When it is necessary to administer medication to a patient, one has the option of either making a keyboard entry 26 of either the patient code number or name into the computer memory or by scanning the patient wrist band 34 with a bar code reader. In either event, the computer will provide a printout 32 which will indicate the proper medication, the required dose, the time to administer the medication, together with a photograph of the patient for positive identification, to assure that the proper patient is receiving the prescribed medication at the designated time. As an additional check, the wrist band may be scanned a second time, 36 as the patient takes the medication. In the alternative, the nurse may provide another coded input to the computer when the medicaction has been administered to the patient, to indicate that the patient has, in fact, taken the medication. In either situation, the computer will record the time the medication was administered.

While the foregoing exegesis has been set forth in terms of a medication dispensing identifier method for maintaining a medical surveillance of dispensed medication, I do not wish to be so limited. It will also also now be apparent that the method I described has equal applicability to monitoring stockrooms, and the like, or any other situation where it is desired to monitor and/or maintain surveillance over any material that is being dispensed to specific people, on a regular basis.

What I claim is:

1. A method of dispensing medication and for maintaining a close surveillance over both a patient for whom the medication is solely intended and over a prescribed medication to be dispensed, comprising the steps of:

initially recording and storing a photograph of the patient for whom the medication is solely intended;

initially recording and storing vital information relating to the prescribed patient medication and the dosage thereof;

providing label means;

creating and imprinting the label with:
   (a) a visual record of the stored photograph; and
   (b) a printout of the stored vital patient information;

providing a container for transporting to the patient, the prescribed medication as described in the printout;

affixing the imprinted label to the container; and comparing the photograph imprinted on the label with the patient to whom the medication is to be dispensed, before any medication is dispensed.

2. The method of dispensing medication set forth in claim 1, wherein, the steps of recording and storing the photograph and vital patient information comprises:

storing the photograph and vital patient information for subsequent retrieval in a computer system; and computer generating, on demand, a uniquely distinctive, machine readable code number, which code number corresponds to the previously stored patient photograph and vital information.

3. The method of dispensing medication set forth in claim 2, comprising the further steps of:

fixing an identifier band around a limb of the patient;

the band having the uniquely distinctive, machine readable code number imprinted thereon;

the code number corresponding to the photographic likeness and vital patient information stored in the computer system; and scan reading the code number on the identifier band, to recreate on a label the photograph and information stored in the computer system.

4. The method of dispensing medication of claim 3, comprising the further steps of:

affixing the label to a container selected from the group consisting of a vial, a patient medication card, a divider card, a patient chart, a patient records card, a medication storage segment, or any combination thereof, assuring the patient and the person administering the medication that the medication indicated in the vital patient information is being given to the patient appearing in the photograph on the label.

* * * * *